(12) United States Patent
Smith et al.

(10) Patent No.: US 10,893,983 B2
(45) Date of Patent: Jan. 19, 2021

(54) METHOD FOR DRESSING A WOUND

(75) Inventors: Jan G. Smith, Askim (SE); Peter Robertsson, Lomma (SE)

(73) Assignee: Abigo Medical AB, Gothenburg (SE)

( * ) Notice: Subject to any disclaimer, the term of this patent is extended or adjusted under 35 U.S.C. 154(b) by 1091 days.

(21) Appl. No.: 12/592,710

(22) Filed: Dec. 1, 2009

(65) Prior Publication Data
US 2010/0160853 A1 Jun. 24, 2010

Related U.S. Application Data

(60) Provisional application No. 61/200,721, filed on Dec. 3, 2008.

(51) Int. Cl.
*A61F 13/00* (2006.01)

(52) U.S. Cl.
CPC .. *A61F 13/00068* (2013.01); *A61F 13/00063* (2013.01); *A61F 2013/0054* (2013.01); *A61F 2013/0091* (2013.01); *A61F 2013/00174* (2013.01); *A61F 2013/00319* (2013.01); *A61F 2013/00536* (2013.01)

(58) Field of Classification Search
CPC .. A61M 1/0088; A61M 27/00; A61M 1/0023; A61M 2205/7536; A61M 1/00; A61F 13/00068; A61F 13/0206; A61F 13/0209; A61F 13/0216; A61F 13/022; A61F 2013/00536; A61F 2013/00319; A61F 2013/00174
USPC ...... 604/23, 315, 304–305, 308, 313, 46–47
See application file for complete search history.

(56) References Cited

U.S. PATENT DOCUMENTS

| | | | |
|---|---|---|---|
| 2,229,061 A | * | 1/1941 | Eustis ............. A61L 15/28 260/DIG. 47 |
| 4,211,227 A | | 7/1980 | Anderson et al. |
| 4,275,721 A | | 6/1981 | Olson |
| 4,617,326 A | * | 10/1986 | Bjornberg ........ A61F 13/00 424/443 |
| 4,642,108 A | | 2/1987 | Sustmann |
| 4,643,180 A | | 2/1987 | Feld et al. |
| 4,643,181 A | | 2/1987 | Brown |

(Continued)

FOREIGN PATENT DOCUMENTS

| | | | |
|---|---|---|---|
| CN | 87101823 B | * 10/1988 | ............ A61F 13/00 |
| DE | 100 20 989 A1 | 4/2000 | |

(Continued)

OTHER PUBLICATIONS

Jeffery, Steven "Non-adherent and flexible—using Cutimed Sorbact as a filler and liner with NPWT" *Journal of Wound Care* 23(5 Suppl):S3-S15 (2014).

(Continued)

*Primary Examiner* — Nathan R Price
*Assistant Examiner* — Weng Lee
(74) *Attorney, Agent, or Firm* — Myers Bigel, P.A.

(57) ABSTRACT

A method for dressing a wound is provided including providing a wound dressing pad of hydrophobic fabric that is treated to bind microorganisms; placing the hydrophobic fabric so that it faces the wound; and applying negative pressure therapy to the wound dressing so that microorganisms in the wound surface adhere to the dressing through hydrophobic interaction. The negative pressure therapy may be alternated with hyperbaric oxygen treatments of the wound dressing.

19 Claims, 2 Drawing Sheets

(56) References Cited

U.S. PATENT DOCUMENTS

| | | | |
|---|---|---|---|
| 4,655,756 A | 4/1987 | Fawkes | |
| 4,678,704 A | 7/1987 | Fellows | |
| 4,832,009 A | 5/1989 | Dillon | |
| 5,098,417 A | 3/1992 | Yamazaki et al. | |
| 5,380,294 A | 1/1995 | Persson | |
| 5,447,492 A | 9/1995 | Cartmell et al. | |
| 5,464,610 A | 11/1995 | Hayes, Jr. et al. | |
| 5,497,789 A | 3/1996 | Zook | |
| 5,498,416 A | 3/1996 | Carsenti-Etesse et al. | |
| 5,700,742 A | 12/1997 | Payne | |
| 5,707,736 A | 1/1998 | Levy et al. | |
| 5,753,256 A | 5/1998 | Cordes et al. | |
| 5,817,325 A | 10/1998 | Sawan et al. | |
| 5,856,248 A | 1/1999 | Weinberg | |
| 5,941,840 A | 8/1999 | Court et al. | |
| 6,037,431 A | 3/2000 | Shioji et al. | |
| 6,160,196 A * | 12/2000 | Knieler | A61L 15/42 424/443 |
| 6,369,289 B1 | 4/2002 | Orr, III | |
| 6,416,779 B1 | 7/2002 | D'Augustine et al. | |
| 6,500,539 B1 * | 12/2002 | Chen | A61L 15/26 428/364 |
| 7,576,256 B2 | 8/2009 | Bjornberg et al. | |
| 7,648,488 B2 * | 1/2010 | Smith | A61B 5/445 604/304 |
| 2003/0068331 A1 | 4/2003 | Battaglia et al. | |
| 2004/0082925 A1 | 4/2004 | Patel | |
| 2004/0127831 A1 | 7/2004 | Sigurjonsson | |
| 2004/0161452 A1 | 8/2004 | Petit | |
| 2004/0265362 A1 | 12/2004 | Susilo | |
| 2006/0163149 A1 | 7/2006 | Wadstrom et al. | |
| 2006/0165761 A1 | 7/2006 | Trotter | |
| 2006/0264857 A1 | 11/2006 | Colbert | |
| 2008/0177214 A1 | 7/2008 | Robertsson et al. | |
| 2008/0249485 A1 | 10/2008 | Effing | |
| 2009/0131909 A1 | 5/2009 | Bjornberg et al. | |

FOREIGN PATENT DOCUMENTS

| | | |
|---|---|---|
| EP | 0 162 026 B1 | 10/1990 |
| EP | 0 475 807 A2 | 3/1992 |
| EP | 2 370 035 B1 | 3/2014 |
| WO | WO 92/13577 | 8/1992 |
| WO | WO 2004/017881 A1 | 3/2004 |
| WO | WO 2005/067991 A1 | 7/2005 |
| WO | WO 2007/062024 A1 | 5/2007 |
| WO | WO 2007/073246 A1 | 6/2007 |
| WO | WO 2010/063791 A1 | 6/2010 |

OTHER PUBLICATIONS

Malmsjö et al. "Bacteria and fungus binding mesh in negative pressure wound therapy: A review of the biological effects in the wound bed" *EWMA Journal* 12(3):27-31 (2012).
Malmsjö et al. "Comparison of bacteria and fungus-binding mesh, foam and gauze as fillers in negative pressure wound therapy—pressure transduction, wound edge contraction, microvascular blood flow and fluid" *International Wound Journal* 10:597-605 (2013).
Malmsjö et al. "Use of Bacteria—and Fungus-Binding Mesh in Negative Pressure Wound Therapy Provides Significant Granulation Tissue Without Tissue Ingrowth" *Eplasty* 14:21-32 (2014).
U.S. Appl. No. 61/200,721, Smith et al, Dec. 3, 2008.
Ambrosio et al. "V.A.C. GranuFoam Silver® Dressings: The Only Antimicrobial Silver Foam Dressing Specifically Engineered for Use with V.A.C.® Therapy" *KCI Licensing, Inc.* (10 pages) (2006).
Annex to the summons to oral proceedings corresponding to European Patent No. 2 370 035 (11 pages) (Sep. 25, 2015).
Assignment of U.S. Appl. No. 61/200,721 and Priority Right to Abigo Medical AB (2 pages.) (Oct. 15, 2009).
"Best Practice Statement: Gauze-based Negative Pressure Wound Therapy" *Wounds UK, Aberdeen* (20 pages) (2008).
BSN Medical Product Catalog (155 pages) (2008).
Campbell, Penny E. "Surgical Wound Case Studies With the Versatile 1 Wound Vacuum System for Negative Pressure Wound Therapy" *Journal of Wound Ostomy & Continence Nursing* 33:2-10 (2006).
Covidien "Wound Care Catalog" (56 pages) (2011).
Cutimed® Sorbact® Instructions for use (2 pages) (Oct. 2007).
European Patent Office Communication of a Notice of Opposition corresponding to European Patent Application No. 09764810.9 (8 pages) (dated Jan. 14, 2015).
European Wound Management Association (EWMA) "Position Document: Management of wound infection" (19 pages) (2006).
Kammerlander et al. "An investigation of Cutimede® Sorbact® as an antimicrobial alternative in wound management" *Wounds* 4(2):10-18 (2008).
Ljungh et al. "Using the principle of hydrophobic interaction to bind and remove wound bacteria" *Journal of Wound Care* 15(4):1-6 (2006).
Material Safety Data Sheet: Aquaphor Gauze/Cuticerin Dressings *Smith & Nephew, Inc.* (3 pages) (Dec. 9, 2003).
Meuleneire, Frans "Clinical Experiences of Using the Combination of an Antimicrobial Hydrophobic Dressing Combined With a Foam for Topical Negative Pressure" *EWMA Conference* (1 page) May 20-22, 2009 (Abstract Only).
Notice of Opposition corresponding to European Patent No. EP 2 370 035 (29 pages) (Dec. 22, 2014).
Notice of Recordation of Assignment Document issued by the U.S. Patent and Trademark Office corresponding to U.S. Appl. No. 61/200,721 (2 pages) (Nov. 3, 2009).
NPVVT Wound Filler Sorbact (4 pages) (Date unknown; date from opposing party provided as 2012).
Paglinawan et al. "A comparative study of the influence of different pressure levels combined with various wound dressings on negative pressure wound therapy (NPWT) driver wound healing" *Medela AG, Presented at the European Tissue Repair Society, Malta* (1 page) (Sep. 10-12, 2008).
Preparation for oral proceedings—Instructions to Support Service corresponding to European Patent No. 2 370 035 (2 pages) (Sep. 25, 2015).
Probst, Astrid "Management of a Stab Wound" *Cutimed® Cavity Advanced wound care* (4 pages) (2009).
Response to the Notice of Opposition corresponding to European Patent No. EP2370035 (33 pages) (Aug. 5, 2015).
Search for publication D2 ("management of a stab wound") before Dec. 3, 2009 (1 page) (search conducted Dec. 15, 2014).
Smith, Glenn "Five case studies demonstrating Negative Pressure Wound Therapy using the gauze-based dressing technique" *Talley Group Limited* (2 pages) (2008).
Sorbact "Green Wound Healing" *Product Leaflet* (4 pages) (Date unknown; date from opposing party provided as 2008).
Sorbact® Guide "Guidance in the treatment of unclean, exuding, colonized, infected wounds and fungal infections" Product Leaflet (2 pages) (2008).
Sorbact & NPWT Case Study—Transmetatarsal Amputee (1 page) (Sep. 21, 2009).
Summons to attend oral proceedings pursuant to Rule 115(1) EPC corresponding to European Patent No. 2370035 (4 pp.) (Sep. 25, 2015).
United States Department of Health & Human Services: Food and Drug Administration "510(k) Notification Summary" *Premarket Notification Submitted by Abigo AB* (8 pages) (Apr. 19, 2007).
United States Code § 360c "Classification of devices intended for human use" *Title 21 13 Food and Drugs* pp. 238-245 (2002).
Voggenreiter et al. "Wundtherapie" (6 pages) (2004).
"Affidavit to be submitted in the European Patent Office in Munich in support of the Opposition proceedings against European Patent EP 2 370 035" *Annex D11a* (12 pages) (Aug. 4, 2016).
Annex 1 to an Opposition Letter corresponding to Opposition proceedings against European Patent No. 2 370 035 (1 page) (Aug. 4, 2016).
Annex 2 to an Opposition Letter corresponding to Opposition proceedings against European Patent No. 2 370 035 (3 pages) (Aug. 4, 2016).

(56) References Cited

OTHER PUBLICATIONS

Baranoski et al. "Wound Care Essentials: Practice Principles" *Lippincott Williams & Wilkins* document D39 corresponding to Opposition proceedings against European Patent No. 2 370 035 (4 pages) (2004).
Berger et al. "Principles and Practice of Palliative Care and Supportive Oncology" *Lippincott Williams & Wilkins* document D37 corresponding to Opposition proceedings against European Patent No. 2 370 035 (3 pages) (2007).
Bryant et al. "Acute & Chronic Wounds: Current Management Concepts" Chapter 20, p. 435 (2007) document D40 corresponding to Opposition proceedings against European Patent No. 2 370 035.
BSN Medical "Wound Care Product Catalog" document D27 corresponding to Opposition proceedings against European Patent No. 2 370 035 (6 pages) (2007).
Decision of the Opposition Division and Instruction corresponding to European Patent No. 2 370 035 (1 page) (Sep. 26, 2016).
Decision Revoking the European Patent corresponding to European Patent No. 2 370 035 (2 pages) (Sep. 26, 2016).
EWMA Journal vol. 9, No. 3 (3 pages) document D11c corresponding to Opposition proceedings against European Patent No. 2 370 035 (2009).
Grounds for the Decision (Annex)—Opposition corresponding to European Patent No. 2 370 035 (9 pages) (Sep. 26, 2016).
Hallern et al. "Cutisorb® Sorbact®—Nonpharmacologic antibacterial therapy in traumatology and surgery" *Medizin & Praxis Infected Wounds* document D31 corresponding to Opposition proceedings against European Patent No. 2 370 035 (8 pages) (2004).
Hallern et al. "Removal of wound bacteria from infected and colonized wounds with Cutisorb® Sorbact®" *Medizin & Praxis Infected Wounds* document D29 corresponding to Opposition proceedings against European Patent No. 2 370 035 (12 pages) (2004).
Hallern et al. "Has Cutisorb Sorbact proved its practical value as an antibacterial dressing?" *Medizin & Praxis Infected Wounds* document D32 corresponding to Opposition proceedings against European Patent No. 2 370 035 (7 pages) (2005).
Hampton, Sylvie "An evaluation of the efficacy of Cutimede® Sorbact® in different types of non-healing wounds" *Wounds UK* 3(4):1-6 (2007) document D28 corresponding to Opposition proceedings against European Patent No. 2 370 035.
Kirby, Michael "Negative Pressure Wound Therapy" *British Journal of Diabetes and Vascular Disease* 7(5):230-234 (2007) document D41 corresponding to Opposition proceedings against European Patent No. 2 370 035.
Lewis, Robert A. "Lewis' Dictionary of Toxicology" (pp. 93-100) document D35 corresponding to Opposition proceedings against European Patent No. 2 370 035 (1998).
Ljungh et al. "A new antibacterial wound dressing without chemically active agent for the care of infected wounds" *Medizin & Praxis Infected Wounds* document D33 corresponding to Opposition proceedings against European Patent No. 2 370 035 (5 pages) (2005).
"Nurse's 3 Minute Clinical Reference" *Lippincott Williams & Wilkins* 2nd Edition document D30 corresponding to Opposition proceedings against European Patent No. 2 370 035 (4 pages) (2008).
"Omni Medical Supply, Inc. Podiatry Catalog 2006" document D38b corresponding to Opposition proceedings against European Patent No. 2 370 035 (41 pages) (2006).
Screenshot of search for "ProCare" on http://link.springer.com/journal/volumesAndIssues/735 document D34a corresponding to Opposition proceedings against European Patent No. 2 370 035 (1 page) (2015).
Screenshot of search for "Nurse's 3 Minute Clinical Reference" on http://www.factsfetch.com document D30a corresponding to Opposition proceedings against European Patent No. 2 370 035 (3 pages) (2015).
Screenshot of search on http://dvd.sagepub.com/content/7/5.toc (1 page) document D41a corresponding to Opposition proceedings against European Patent No. 2 370 035 (2016).
Screenshot of search on http://www.wounds-uk.com/journal/issue/317 (2 pages) document D4a corresponding to Opposition proceedings against European Patent No. 2 370 035 (2016).
Screenshot of search on http://www.wounds-uk.com/journal/issue/315 (2 pages) document D28a corresponding to Opposition proceedings against European Patent No. 2 370 035 (2016).
Screenshot of search on google.de for "Vista NPWT Instruction Manual" (1 page) document D43a corresponding to Opposition proceedings against European Patent No. 2 370 035 (2016).
Screenshot of search with Wayback Machine for "2009 Poster Abstracts" http://www.ewma.org/English/ewwa-conferences/conference-abstracts/2009/2009-poster-abstract.htm document D11b corresponding to Opposition proceedings against European Patent No. 2 370 035 (5 pages) (2015).
Screenshot of search with Wayback Machine for "510(k)s Final Decisions Rendered for Apr. 2007" http://web.archive.org/web/20080709045659/http://www.fda.gov/cdrh/510k/sumapr07.html document D9e corresponding to Opposition proceedings against European Patent No. 2 370 035 (1 page) (2008).
Screenshot of search with Wayback Machine for "Abigo Medical AB product brochures" www.abigo.se/en/brochures.html (1 page) document D9d corresponding to Opposition proceedings against European Patent No. 2 370 035 (2015).
Screenshot of search with Wayback Machine for "Best Practice Statement and Outcome Data for gauze-based Negative Pressure Wound Therapy" http://web.archive.org/web/2008/1201144952/http://www.tallevgroup.com/news/articie/best_practice_statement_and_outcome_data_for_gauze_based_negative_pressure_/ document D6a corresponding to Opposition proceedings against European Patent No. 2 370 035 (1 page) (2008).
Screenshot of search with Wayback Machine for "Ethicon" http://www.ethicon.com document D38a corresponding to Opposition proceedings against European Patent No. 2 370 035 (1 page) (2007).
Screenshot of search with Wayback Machine for "Management of wound infection" www.ewma.orgdocument D7a corresponding to Opposition proceedings against European Patent No. 2 370 035 (1 page) (2007).
Screenshot of search with Wayback Machine for "The Venturi" www.talleygroup.com/talley_medical/negative_pressure/venturi document D15a corresponding to Opposition proceedings against European Patent No. 2 370 035 (1 page) (2008).
Screenshot of search with Wayback Machine on http://www.cutimedsorbact.com/pub.htm (1 page) document D42 corresponding to Opposition proceedings against European Patent No. 2 370 035 (2008).
Schwanke, Dorte "Wundmanagement" (6 pages) document D34 corresponding to Opposition proceedings against European Patent No. 2 370 035 (6 pages) (2008).
Search for "Cutimed Sorbact instruction for use" before Dec. 3, 2008 www.google.de (1 page) (2008).
Search for "Smith & Nephew 59092662 Aquaphor Gauze Nonadherent Dressing—3" x 8", 3/package, Box of 25 dressings" www.woundcareshop.com document D14a corresponding to Opposition proceedings against European Patent No. 2 370 035 (2 pages) (2016).
Search with Wayback Machine for "BSN Medical: Wound Care" www.bsnmedical.com/en/whatwedo/woundcare/page/html document D36 corresponding to Opposition proceedings against European Patent No. 2 370 035 (1 page) (2008).
Search Results for "Sorbact wound dressing" http://www.accessdata.fda.gov document D9f corresponding to Opposition proceedings against European Patent No. 2 370 035 (8 pages) (2016).
Smith & Nephew "Wound Management product catalogue" *Smith & Nephew GmbH* document D14b corresponding to Opposition proceedings against European Patent No. 2 370 035 (44 pages) (Jan. 2007).
Smith & Nephew "Patent Home Care Information" *Smith & Nephew GmbH* document D43 corresponding to Opposition proceedings against European Patent No. 2 370 035 (28 pages) (Jul. 2008).
Stannard et al. "Split-Thickness Skin Graft" *Surgical Treatment of Orthopaedic Trauma* p. 13, document D38 corresponding to Opposition proceedings against European Patent No. 2 370 035 (3 pages) (2007).

(56) References Cited

OTHER PUBLICATIONS

Voggenreiter et al. "Wundtherapie" (1 page) document D8a corresponding to Opposition proceedings against European Patent No. 2 370 035 (2004), p. 35.
Written Submission corresponding to Opposition against European Patent No. 2 370 035 (57 pages) (Aug. 4, 2016).

* cited by examiner

METHOD FOR DRESSING A WOUND

CROSS-REFERENCE TO RELATED APPLICATIONS

This application claims priority from U.S. provisional application Ser. No. 61/200,721, filed Dec. 3, 2008.

BACKGROUND OF THE INVENTION

1. Field of the Invention

The invention herein relates to a wound dressing method, with a hydrophobic fabric, possibly including a mounted absorbent material attached thereto, the hydrophobic fabric facing towards the wound and being capable of binding unwanted microorganisms, used with vacuum or alternating vacuum and hyperbaric oxygen treatments of the wound dressing.

2. Description of the Related Art

One problem in healing of wounds associated with bacterial loads is tissue damage by release of toxins and enzymes, and possible spread of infections to the blood stream. Studies have shown that high tissue counts of microorganisms delay wound healing.

Numerous studies during the last few decades have also shown that bacteria, such as *Staphylococcus aureus* and Group A streptococci, both common wound pathogens, and the yeast *Candida albicans* commonly express profound cell surface hydrophobicity. Several structures which render the cell surface hydrophobic have been defined, like the fimbriae of *E. coli*, which mediate adhesion to the intestinal wall, proteins on *C. albicans*, which have been called "hydrophobins", and lipoteichoic acid in the cell wall of Gram-positive bacteria.

According to the hydrophobic principle of the laws of nature, a system will always struggle towards lowest possible energy consumption. When two water repellent molecules come into collision with each other they will increase the entropy and create disorder. The water molecules that surround the two hydrophobic molecules will force them together by hydrogen bonds between the water molecules although there is no force of attraction between the hydrophobic interactions, and will expel water molecules.

The initial step in infections of the skin and mucosal surfaces is microbial adhesion to wounded tissues. Several microbial components that adhesively bind to specific receptors have been identified, like fimbriae of Gram-negative enteric bacteria. Initial adhesion can be mediated by hydrophobic interactions between microbes and host tissue structures, and also by charge interactions. Binding of extracellular matrix and serum proteins, like fibronectin, collagen and fibrinogen may further enhance colonization of deeper wound tissue.

In wound treatment, after tissue colonization wound microbes multiply, cause tissue damage by release of toxins and enzymes, and even spread to the blood stream. The human body has multiple defense mechanisms of the innate defense system. Also specific antibodies directed against the colonizing microorganism may be active to decrease the number of microorganisms. Numerous studies have shown that high tissue counts of microorganisms delay wound healing. On the other hand, small numbers of bacteria were shown to enhance the wound healing process in rodents by stimulating production of collagen-hydroxyproline.

Conventional treatment of wounds consists of mechanical cleansing with water, buffer solutions or disinfectants to remove bacteria and debris. This is of importance since debris hampers wound healing. The use of oxidizing agents (for example iodine tincture) or antiseptics (for example ointments comprising silver sulphadiazine) have been known for a long time. A number of disadvantages to these methods can be mentioned. For example, bacteria which have died remain in the wound, and wounds cannot be cleaned to remove the active compound reliably after the application, since it spreads in the entire wound. If these active compounds occur freely in the wound, they can also attack cells and substances in the wound fluid which promote wound healing.

Another method of wound treatment is the use of local antibiotics. Microbiologists disapprove of the use of local antibiotics since this is known to induce antibiotic resistance. Also in order to protect an already cleaned wound, including wounds from surgical cuts, various kinds of Band-Aid's, surgical tapes and dressings and the like have been used. Various kinds of cleaning and anti-microbial compounds added to such products been added or suggested for more long time effects.

There are several known inventions relating to methods and materials in wound healing. One such example is the U.S. Pat. No. 6,369,289, which discloses the use of a cellulosic bandage in a method for covering an open wound by contacting the wound with the bandage having a calculated amount of antimicrobial agent. The disclosure of this patent and all other patents referred to herein is incorporated herein by reference. U.S. Pat. No. 4,655,756 relates to a non-woven material treated with a linear polymeric biguanide having a defined formula, or a mixture of, e.g., polyhexamethylene biguanide (PHMB).

Other types of antimicrobial agents are also known. For example, U.S. Pat. No. 5,707,736 discloses a dry, disposable, polymeric product having sustained-release antimicrobial activity that is formed from a polymeric material having an amine salt antimicrobial agent incorporated therein. The polymeric material may be in the form of fibers, sheets, films, and other stable woven, nonwoven and knitted materials. The antimicrobial agents include, e.g., chlorhexidine gluconate and chlorhexidine hydrochloride. Several similar uses of dressings combining antimicrobial compounds are known.

U.S. Pat. No. 4,643,181 also describes a surgical dressing and a process for making a surgical dressing. The dressing comprises a substrate coated on one surface with a solvent-based skin contact adhesive of defined thickness, the adhesive having distributed therein particles of antimicrobial substances.

U.S. Pat. No. 4,678,704 describes an impregnated fabric material comprising a fabric substrate to which has been applied an active cationic impregnant along with an anionic indicator dye in combination with a further cationic component, wherein the dye bonds to the further cationic component more readily than to the substrate and the further cationic component competes with the impregnant for bonding to the dye. The cationic impregnant may be a polymeric biguanide.

U.S. Pat. No. 5,098,417 relates to a wound dressing for systemic administration of a physiologically- or biologically-active agent by controlled release of the agent into such wound. The wound dressing comprises a substrate in the form of a fabric or cloth, at least a portion of which is cellulosic, which has been chemically modified to convert hydroxyl groups in the cellulosic portion to ionic-adsorbing sites, an ionic form of a physiologically- or biologically-active agent (which includes antibacterial agents) adsorbed in the substrate. The ionic bonds hold the agent temporarily to the substrate for controlled release therefrom in proportion to the amount of exudate in contact with the substrate and are formed by adsorbing the agent on the substrate at room temperature. The ionic bonds are disassociated upon contact with body exudate from wounds thereby to release the physiologically- or biologically-active agent in an amount in proportion to the amount of exudate in contact with the substrate.

U.S. Pat. No. 5,498,416 relates to a process for protection of prostheses, implants and/or catheters, and other temporary or permanent implantable materials against bacterial colonization and infection. An infection-resistant device is disclosed that in aqueous medium is capable of progressively releasing an amount of an antibacterial substance fixed to the device, the amount being effective to prevent bacterial contamination of the device. Devices are described to include urinary catheters, probes, vascular and intraarterial catheters, cardiacal valvular prostheses, arterial prostheses, cardiac simulators, orthopedic prostheses, ocular or dental implants, shunts that are connecting two segments of the circulatory system, and suture thread.

U.S. Pat. No. 5,700,742 relates to a method of treating a textile material to inhibit microbial growth, which comprises applying to the textile material an oligo or polymeric biguanide or salt thereof with an inorganic acid or an organic acid having a pK value above 4.5 followed by a strong organic acid having a pK value below 4.5 and free from any aliphatic or oxyalkylene chain containing 12 or more carbon atoms. A textile material treated in accordance with the claimed method is also disclosed.

U.S. Pat. No. 5,856,248 relates to cellulose fibers and products comprising cellulose fibers treated to absorb body secretions while substantially decreasing microbial growth, the fibers being chemically modified in a two-stage process comprising a first stage treatment with a water soluble salt of a transition metal and an alkali and a second stage treatment with a solution of a bisbiguanide compound, thereby forming a bond between the cellulose fibers, the transition metal and the compound. The process may utilize a rinsing step to neutral pH between the two aforementioned stages.

U.S. Pat. No. 5,817,325 relates to an article of manufacture having disposed on a surface thereof a contact-killing, non-leaching antimicrobial coating which kills microorganisms upon contact. The coating comprises an organic polycationic polymer matrix immobilized on the surface having bound or complexed thereto a surface-accessible antimicrobial metallic material such that the antimicrobial material does not release biocidal amounts of elutables into the surrounding environment.

Other patents relate to the so called SORBACT products, which are folded dressing compositions including a hydrophobic fabric and a hydrophilic, liquid-absorbing material. U.S. Pat. No. 4,617,326 describes this principle.

Further, U.S. Pat. No. 6,160,196 relates to the Sorbact principle but adds thereto an antimicrobial active compound which is adapted to prevent infections from the outside of the pad. The antimicrobial compound is not released into the wound. U.S. Pat. No. 4,211,227 discloses a non-woven surgical sponge material comprising a layered fabric having an inner core or a substantially hydrophilic material disposed adjacent at least one outer or surface layer, or between a pair of outer layers, of a substantially hydrophobic material. The sponge material is bonded by passing the material through rolls engraved in a pattern of lands and grooves such that a repeating pattern of three degrees of compression are imposed on the material. However, this sponge does not use a hydrophobic material binding bacteria to any great extent, nor does it have any backing which is visually transparent, semi-permeable and self-adhesive.

Further, there are several wound dressing products on the market containing absorbent pads, but without any antimicrobial compounds or microbial binding materials. Such products include Tegaderm® and Tegaderm® IV by 3M, (St. Paul, Minn. 55144-1000, U.S.A.) and OpSite Post-Op by Smith&Nephew (Memphis, Tenn. 38116, U.S.A.).

Several patents and other publications are related to the so called NPWT (negative pressure wound therapy), for example one wound care system disclosed in WO 2007/062024 is an apparatus capable of administering localized negative pressure therapy to a covered wound using a negative pressure source and a drain line for removing exudates from the wound, alternating with hyperbaric oxygen therapy. Negative pressure therapy is the controlled application of sub-atmospheric pressure to a wound, using a vacuum or suction device to remove exudates from the wound. Hyperbaric oxygen therapy is the controlled application to a wound of pressures greater than atmospheric pressure to promote new cell growth and increase metabolic activity of the cells. The apparatus of this patent application is also capable of administering localized hyperbaric fluid therapy to the wound using a fluid source and a supply line for hyperbaric fluid therapy. The system for wound care in this patent is designed for alternating applications of vacuum and hyperbaric wound treatments to a wound site.

What characterizes the art in the field of the invention is that developments and inventions are most often related to various fibrous materials and pads with added antimicrobial substances to be used with a separate bandage or fastened over wounds, using for example, surgical tape or various dressings or alternatively used with different systems to create negative pressure and possibly also hyperbaric conditions at the wound site.

Utilizing the Sorbact principle discussed above, products such as the Sorbact pad consist of acetate gauze and cotton gauze treated with the fatty acid ester DACC (dialkyl carbamoyl chloride) or dioctadecyl-carbamoyl chloride or an alkyl ketene dimer (AKD). This provides Sorbact pads with a strong hydrophobic property. When the Sorbact pad comes in contact with pathogenic microorganisms in the wound surface, the microorganisms adhere to the pad through hydrophobic interaction. The method is based on the principle that two hydrophobic surfaces bind to each other, when coming into physical contact. The pad can optionally be rendered cation active by means described in U.S. Pat. No. 4,617,326 and U.S. Patent application 2006/0129080 or the by application of cationic dyes known in the art. The Sorbact pad consists of one or two components. The first component has one or more liquid permeable layers of a hydrophobic, bacteria adsorbing, physiologically innocuous material containing a woven or nonwoven hydrophilic fabric. The fabric has been rendered hydrophobic by chemical treatment with a compound containing hydrophobic groups. The second optional component consists of one or more layers of a hydrophilic, liquid absorbing, physiologically innocuous material. The hydrophilic liquid absorbing material effects a liquid flow by suction of exudate from the wound. If the microorganisms exhibit hydrophobic surface structures they will accompany this flow of liquid and come in contact with the hydrophobic component and bind to it.

The Sorbact acetate gauze can also be used by itself without any absorption material layer.

Even if the traditional Sorbact product solves an important problem of reducing the number of microorganisms in a wound without using chemicals or antibiotics, it has still some disadvantages when used as a wound dressing. It has been showed that a good contact between the wound and the hydrophobic and possible cationic fabric is essential for an efficient attachment/binding of the unwanted microbes of the wound. Many wound surfaces are not flat or even, which makes it difficult to get a sufficiently good contact between the hydrophobic and possible cationic fabric and the wound.

Therefore the invention herein was made to address the above problems. It was surprisingly shown that the effect of the Sorbact material in binding microorganisms increased substantially when used with vacuum or with alternating vacuum and hyperbaric oxygen treatments of the wound dressing. The increased effect of the Sorbact material in binding microorganisms, when applying vacuum or alternating vacuum and hyperbaric oxygen treatments to the wound dressing is caused by better contact between the Sorbact gauze and the wound and the better flow of exudate through the Sorbact material.

It is an object of the invention herein to provide a product ideal for the treatment of wounds and a method of making this product. It is a further object of the invention to provide a product that protects the wound, absorbs exudates and removes excess exudates, reduces the number of pathogenic microorganisms, and aids in wound recovery, without using antimicrobial substances.

Other objects and advantages will be more fully apparent from the following disclosure and appended claims.

SUMMARY OF THE INVENTION

The invention herein relates to a wound dressing method using a product with a hydrophobic fabric, possibly including a mounted absorbent material, attached thereto, facing towards the wound and being capable of binding unwanted microorganisms, used with vacuum or alternating vacuum and hyperbaric oxygen treatments of the wound dressing.

The method of the invention protects the wound, absorbs exudate and reduces the number of pathogenic microorganisms, without using antimicrobial substances, and further utilizes the vacuum treatment to remove excess exudates and the hyperbaric oxygen treatment to enhance wound healing. The method of the invention provides a wound dressing utilizing the Sorbact principle together with negative and positive pressure application to the wound dressing.

Other objects and features of the inventions will be more fully apparent from the following disclosure and appended claims.

DETAILED DESCRIPTION OF THE INVENTION AND PREFERRED EMBODIMENTS THEREOF

Figure 1:
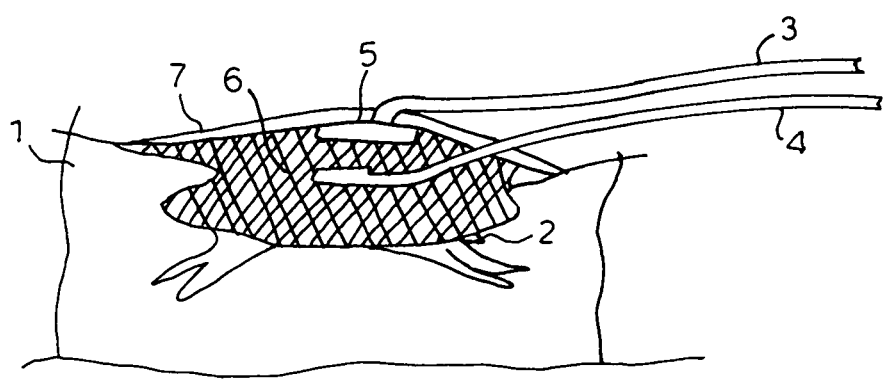
FIG. 1 shows an overview of the treated wound site according to the invention herein.

The product of the invention is ideal for treatment of wounds. It protects the wound, removes exudate and reduces the number of pathogenic microorganisms, without using antimicrobial substances. In the method of the invention, the wound is treated with vacuum and possibly alternating hyperbaric oxygen treatments using a wound dressing based on the Sorbact principle discussed above, for example, products such as the Sorbact pad consist of folded acetate gauze and cotton gauze treated with the fatty acid ester DACC (dialkyl carbamoyl chloride) or dioctadecyl-carbamoyl chloride or an alkyl ketene dimer (AKD) so that the Sorbact pads have a strong hydrophobic property and pathogenic microorganisms in the wound surface adhere to the pad through hydrophobic interaction. The pad can optionally be rendered cation active. Such pads have possibly two primary components, the first of which has one or more liquid permeable layers of a hydrophobic and possible cationic, bacteria-adsorbing, physiologically innocuous material containing a woven or nonwoven hydrophilic fabric. The fabric has been rendered hydrophobic by chemical treatment with a compound containing hydrophobic groups. The optional second component consists of one or more layers of a hydrophilic, liquid absorbing, physiologically innocuous material. The hydrophilic liquid-absorbing material effects a liquid flow by suction of exudate from the wound. If the microorganisms exhibit hydrophobic surface structures they will accompany this flow of liquid and come in contact with the hydrophobic component and bind.

In its basic embodiment the wound dressing used in the invention herein is a bacteria-adsorbing composition in water-insoluble form which includes a first component comprising one or more liquid permeable layers of a powerfully hydrophobic, bacteria adsorbing, physiologically innocuous material comprising a woven or non-woven hydrophilic fabric, which has been rendered hydrophobic by chemical treatment with a compound containing hydrophobic groups, and a second component comprising one or more layers of a hydrophilic, liquid absorbing, physiologically innocuous material, at least one layer of hydrophilic material being located externally of at least part of the hydrophobic material as viewed from the surface to be treated, as set forth in U.S. Pat. No. 4,617,326, the disclosure of which is incorporated herein, used together with vacuum or alternating vacuum and hyperbaric oxygen treatments of the wound dressing supplied from an apparatus for the treatment of a wound on a patient. The apparatus includes a drain line configured for attachment to a negative pressure source and for removing exudate from the wound; a supply line configured for attachment to a fluid source and for supplying fluid to the wound; and a controller. The controller is configured to cause negative pressure therapy to be administered to the wound via the drain line. The controller is further configured to optionally cause hyperbaric fluid therapy, for example using oxygen, to be administered to the wound via the supply line. The controller is further configured to cause hyperbaric fluid therapy to be administered to the wound at an absolute pressure of at least approximately 1.5 atmospheres via the supply line.

A wound treatment apparatus that includes a drain line configured for attachment to a negative pressure source and for removing exudates from the wound, for example the system disclosed in WO 2007/062024 or a similar system, can be used. The apparatus further includes a supply line configured for attachment to a fluid source and for supplying fluid to the wound and a controller. The controller is configured to cause negative pressure therapy to be administered to the wound for a first time period via the drain line, and cause hyperbaric fluid therapy to be administered to the wound for a second time period via the supply line, wherein the first time period is approximately two to three times as long as the second time period. The apparatus further includes a controller that is configured to cause negative pressure therapy to be administered to the wound via the drain line, and optionally to cause hyperbaric fluid therapy to be administered to the wound at via the supply line. The controller is further configured to control the administration of negative pressure therapy and hyperbaric fluid therapy such that the administration of negative pressure therapy and hyperbaric fluid therapy is cyclical and the hyperbaric fluid therapy alone or together is administered to the wound for no more than 30 minutes during each cycle. The negative pressure therapy and hyperbaric fluid therapy may be administered intermittently. The fluid source may be configured to supply a constant flow of fluid such that the administration of negative pressure therapy is accomplished by activating the negative pressure source and the administration of hyperbaric fluid therapy is accomplished by deactivating the negative pressure source.

The administration of negative pressure therapy may also be accomplished by activating the negative pressure source and reducing the flow of fluid from the fluid source, or by not having any flow from a fluid source. Similarly, the administration of hyperbaric fluid therapy may be accomplished by deactivating the negative pressure source and increasing the flow of fluid from the hyperbaric fluid source. While each of the negative pressure therapy and the hyperbaric fluid therapy could potentially be administered to the wound 2 for hours before alternating to the other therapy, it is presently preferred that the controller 9 cause negative pressure therapy to be administered to the wound 2 for relatively short periods of time. For example, negative pressure therapy may be administered for approximately 20-180 seconds before moving on to hyperbaric fluid therapy or to non-therapy in the event that the apparatus is set to intermittently apply only negative pressure therapy. Similarly, the controller 9 may cause hyperbaric fluid therapy to be administered to the wound 2 for approximately 10-60 seconds before moving on to negative pressure therapy or to non-therapy in the event that the apparatus is set to intermittently apply only hyperbaric pressure therapy.

As will be understood by those of skill in the art, the administration of negative pressure therapy generally involves exposing the wound 2 to pressures of less than 1 atmosphere. The pressures employed during negative pressure therapy may include absolute pressures ranging from approximately 0 mm Hg to approximately 300 mm Hg. Preferably, the absolute pressure ranges from approximately 60 mm Hg to approximately 160 mm Hg during the administration of negative pressure therapy.

FIG. 1 shows an example overview of the treated wound site according to the invention herein, where: the skin 1 of a patient, has a wound 2, to be treated by the invention herein, using the woven Sorbact pad 6, on top of the wound 2, and a drain line 4 on top of the Sorbact pad 6, and an optional drain device 5 fixed to the end of the drain line 4, and an optional supply line 3 on top and everything under a sealing material 7 to make the negative pressure and hyperbaric treatment possible.

Figure 2:
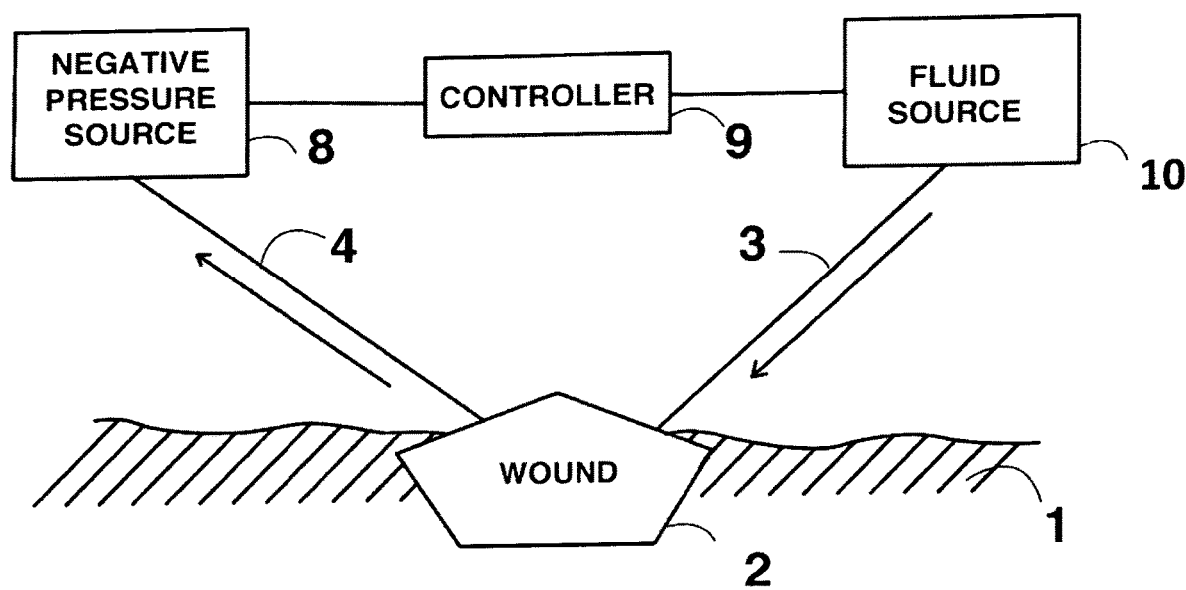
FIG. 2 shows a schematic set-up of a system of the invention herein.

The system for supplying the negative pressure and fluids can be a portable unit as disclosed above or fixed bedside installations for suction and oxygen in hospitals can be used together with a controller and tubing according to FIG. 2, where the wound 2 is dressed according to FIG. 1 and connected to the fluid-source 10, via the supply-line 3 and to the negative pressure source 8, via the drain-line 4 and the negative pressure source 8 and fluid source 10 are controlled by the controller 9.

Other objects and features of the inventions will be more fully apparent from the following examples and appended claims.

Example 1

Manufacture of Wound Dressing Product

In this example, a standard wound dressing is manufactured based on the invention in the following manner:
Materials: (From Inside-Out)

| LAYER | COMMERCIAL PRODUCT NAME | MANUFACTURER |
| --- | --- | --- |
| 1. Hydrophobic layer | Green Cellulose Acetate woven prepared according to U.S. Pat. No. 4,617,326 | ABIGO Medical AB Sweden |
| 2. Optional Adhesive | National 505E | National Starch & Chemical Ltd., United Kingdom |
| 3. Optional Absorbent material | (Airlaid) Concert MH080.104.P000 | Concert GmbH, Falkenhagen, Germany |

A. The hydrophobic layer is preferably produced according to U.S. Pat. No. 4,617,326 by applying to a cellulose acetate fabric an amount of dioctadecyl carbamoyl chloride DACC or AKD as disclosed in this patent making a covalent bond between the materials. The acetate fabric is on rolls of 50 m length and at a width of 1 m, and taken as such to the next step.

B. The optional bonding of the hydrophobic layer with the absorbent layer is made in a machine for the purpose, having a suitable applicator for the hot-melt, a slot applier, and heated rolls for the bonding of the two materials, so called nip rolls, as is known in the art. In order to minimize the risk for the adhesive to bleed through the surface layer it is preferable to put the hot melt layer on the absorbent layer. In prior test runs it was found that the risk for the adhesive to bleed through the hydrophobic cellulose acetate layer increases dramatically if the amount of adhesive is >10 $g/m^2$. Decreasing the amount of adhesive, however, reduces the lamination strength. The ideal amount of adhesive is between 7-10 $g/m^2$. In our prior test runs we found a hot melt temperature of 150 degrees C. to work well together with pre heated nip rolls.

Test of Lamination Strength:

The test sample is placed in water solution with 0.9% NaCl or defibrillated sheep blood for one hour. The layers are separated from each other and the lamination strength is measured. If possible it should be at least 10 gram/cm, but preferably >20 gram/cm width Because it can sometimes be difficult to get hold of the layers in order to separate them, a knife or tweezers with sharp edges may be used, or the sample may be prepared prior to the water test by separating the layers from each other by leaving flaps to grab.

Other Tests:

Adhesive bleeding through the green cellulose acetate woven fabric is tested by pressing samples of the laminated material surface layer (green woven material) hard against each other. Only a minor sticking is acceptable.

Blood clotting is tested by application of 0.3 ml of defibrillated sheep blood on top of the lamination. The blood should easily pass through the green cellulose acetate woven layer and leave only small amounts of blood on the surface.

After the bonding process of the hydrophobic acetate layer and the absorbing layer, the now bonded materials are still in a roll form, which is taken to the cutting step.

Example 2

Use of the New Dressing Product to Bind Pathogens in a Liquid Drench Without Applying Vacuum Material: Wound dressing as described in Example 1
Bacterial strains: *Staphylococcus aureus* Newman, *Pseudomonas aeruginosa* 510, *Enterococcus faecalis*, *Candida albicans*

Isolates were cultured on agar with 5% horse erythrocytes in 5% $CO_2$ atmosphere at 37° C. Suspensions were made in phosphate-buffered saline (PBS, 0.02 M sodium phosphate and 0.15 M sodium chloride, pH 7.2) at $10^9$ bacterial cells/ml, $10^7$ fungal cells/ml or indicated concentration.

The dressing was cut in 1 cm$^2$ pieces. Incubation was made in 24 well polymer plates. 1 ml of suspension was added to each dressing. The plates were placed on a rotary shaker at very low speed. Incubation was performed at room temperature for the indicated time. After incubation, dressings were rinsed in PBS several times, and then put in 2.5% TCA (tricarboxylic acid).

The ATP content was measured in a luminometer (LKB Wallac). Controls: the number of adhered bacteria (CFU/ATP) was normalized against the number of total added bacteria (CFU/ATP), and the blank (no bacteria, only EDTA-Tris buffer) was the ATP value control.

Results:
*S. aureus* >$10^5$ cells adhered during 30 sec, 1, 5 and 10 minutes, and then increased to $10^6$ cells after 2 hrs. Some multiplication occurred during the following 24 hrs to reach $5 \times 10^6$ cells/cm$^2$.

*P. aeruginosa* Around $10^6$ cells adhered during 30 s, 1, 5 and 10 min, and then increased during 30 and 60 min incubation to reach $10^7$ cells/cm$^2$ after 2 hrs incubation. No multiplication of adhered bacteria occurred during the following 24 hrs.

The maximal adsorption was when $5 \times 10^9$ cells of *S. aureus* were added and $10^8$ cells adhered; for *P. aeruginosa*, $10^8$ cells adhered out of $10^{9.5}$ added; and for *E. faecalis*, $8 \times 10^6$ out of $5 \times 10^{10}$ added. For *C. albicans* the slope levels off, and $10^5$ cells adhered out of $10^{7.5}$ added.

Conclusion: Under ideal conditions, the test dressing with the hydrophobic layer, such as this liquid drench, is a good adsorber of different important and potential pathogens in wound healing.

Example 3

Test of the New Dressing on a Rough Surface Without Applying Vacuum

A standardized pig wound model is used (BMC Surg. 2008; 8: 5. Hirsch et al; Enhanced susceptibility to infections in a diabetic wound healing model) and the experimental protocol of Example 2. The maximal adsorption to the Sorbact is measured after 2 hours. When $10^9$ cells of *S. aureus* are added, $10^6$ cells adhere, for *P. aeruginosa* $10^5$ cells adhere out of $10^{9.5}$, and for *E. faecalis* $1 \times 10^5$ cells out of $5 \times 10^{10}$ adhere. For *C. albicans*, $10^3$ cells adhere out of $10^7$ added.

Example 4

Application of Vacuum/Suction and Hyperbaric Pressure

The application of vacuum/suction to the wound dressing discussed above is preferably according to WO 2007/062024 (published May 31, 2007), the disclosure of which is incorporated herein, or methods known in the art that accomplish the same result(s). In particular, the apparatus used therefore preferably includes a drain line that attaches to a negative pressure source, giving 40 mmHg to approximately 120 mmHg negative pressure so that exudates may be removed from a wound. The vacuum level should never be painful, if the patient report discomfort, reduce the under-pressure. An example of one such portable pump is the PROSPERA PRO-I (Prospera Inc, 2831 Bledsoe Street Fort Worth, Tex. 76107, U.S.A.) A controller of this pump, or comparable thereto, controls the administration of the negative pressure therapy.

Example 5

Test of the New Dressing and Vacuum on a Rough Surface

The same experimental set up as in example 3 is used but now combining the Sorbact pad with vacuum as in example 4. The maximal adsorption to the Sorbact pad is measured after 2 hours. When $5 \times 10^9$ cells of *S. aureus* are added, $10^8$ cells adhere, for *P. aeruginosa* $10^7$ cells adhere out of $10^{9.5}$, and for *E. faecalis* $10^7$ out of $10^{10}$. For *C. albicans*, $10^6$ cells adhere out of $10^7$ added.

While the invention has been described with reference to specific embodiments, it will be appreciated that numerous variations, modifications, and embodiments are possible, and accordingly, all such variations, modifications, and embodiments are to be regarded as being within the spirit and scope of the invention.

What is claimed is:

1. A method of treating a wound, comprising:
   a) providing a wound dressing consisting of a hydrophobic fabric that is treated to bind microorganisms through hydrophobic interaction, wherein the hydrophobic fabric is a cellulose acetate gauze treated with a compound containing hydrophobic groups selected from the group consisting of dialkyl carbamoyl chloride, dioctadecyl carbamoyl chloride and alkyl ketene dimers, and wherein the wound dressing does not contain an antimicrobial substance;
   b) placing the hydrophobic fabric so that it faces the wound; and
   c) applying negative pressure therapy to the wound dressing, thereby treating the wound.

2. The method of claim 1, further comprising alternating the negative pressure therapy with hyperbaric oxygen treatments of the wound dressing.

3. The method of claim 1, further comprising providing a drain line configured for attachment to a negative pressure source and for removing exudate from the wound; a supply line configured for attachment to a fluid source and for supplying fluid to the wound; and a controller configured to cause negative pressure therapy to be administered to the wound via the drain line.

4. The method of claim 3, wherein the controller is further configured to cause hyperbaric fluid therapy to be administered to the wound via the supply line.

5. The method of claim 4, wherein the controller is further configured to cause hyperbaric fluid therapy to be administered to the wound at an absolute pressure of at least approximately 1.5 atmospheres via the supply line.

6. The method of claim 4, wherein the hyperbaric fluid therapy utilizes oxygen.

7. The method of claim 4, wherein the controller is further configured to control the administration of negative pressure therapy and hyperbaric fluid therapy such that the administration of negative pressure therapy and hyperbaric fluid therapy is cyclical and the hyperbaric fluid therapy alone or together is administered to the wound for no more than 30 minutes during each cycle.

8. The method of claim 4, wherein the negative pressure therapy and hyperbaric fluid therapy are administered intermittently.

9. The method of claim 4, wherein the fluid source is configured to supply a constant flow of fluid such that the administration of negative pressure therapy is accomplished by activating the negative pressure source and the administration of hyperbaric fluid therapy is accomplished by deactivating the negative pressure source.

10. The method of claim 4, wherein the administration of negative pressure therapy is accomplished by activating the negative pressure source and reducing the flow of fluid from the fluid source.

11. The method of claim 4, wherein the administration of negative pressure therapy is accomplished by not having any flow from the fluid source.

12. The method of claim 4, wherein the administration of hyperbaric fluid therapy is accomplished by deactivating the negative pressure source and increasing the flow of fluid from the hyperbaric fluid source.

13. The method of claim 4, wherein the negative pressure and fluids are supplied by a portable unit.

14. The method of claim 1, wherein negative pressure therapy is administered for about 20-180 seconds followed by hyperbaric fluid therapy, or negative pressure therapy is followed by non-therapy to provide intermittent negative pressure therapy.

15. The method of claim 1, wherein negative pressure therapy is administered for about 10-60 seconds followed by hyperbaric fluid therapy, or negative pressure therapy is followed by non-therapy to provide intermittent negative pressure therapy.

16. The method of claim 1, wherein the administration of negative pressure therapy comprises exposing the wound pressures ranging from about 60-160 mm Hg.

17. The method of claim 1, wherein applying negative pressure therapy to the wound dressing increases the binding of microorganisms to the hydrophobic fabric.

18. The method of claim 1, further comprising placing a sealing material on top of the wound dressing and optionally over a drain line and a supply line.

19. The method of claim 1, wherein the hydrophobic fabric is treated with dioctadecyl carbamoyl chloride or alkyl ketene dimers.

* * * * *